United States Patent
Rögner et al.

(10) Patent No.: US 9,949,425 B2
(45) Date of Patent: Apr. 24, 2018

(54) APPARATUS FOR IMPINGING BULK MATERIAL WITH ACCELERATED ELECTRONS

(71) Applicant: Fraunhofer-Gesellschaft zur Förderung der angewandten Forschung e.V., Munich (DE)

(72) Inventors: Frank-Holm Rögner, Dresden (DE); André Weidauer, Dresden (DE); Gösta Mattausch, Ullersdorf (DE); Jörg Kubusch, Dresden (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 0 days.

(21) Appl. No.: 15/101,752

(22) PCT Filed: Nov. 12, 2014

(86) PCT No.: PCT/EP2014/074378
§ 371 (c)(1),
(2) Date: Jun. 3, 2016

(87) PCT Pub. No.: WO2015/086246
PCT Pub. Date: Jun. 18, 2015

(65) Prior Publication Data
US 2016/0374261 A1    Dec. 29, 2016

(30) Foreign Application Priority Data
Dec. 9, 2013 (DE) .................. 10 2013 113 688

(51) Int. Cl.
*A01C 1/08*    (2006.01)
*B01J 8/12*    (2006.01)
(Continued)

(52) U.S. Cl.
CPC ............... *A01C 1/08* (2013.01); *A61L 2/087* (2013.01); *A61L 2/26* (2013.01); *B01J 8/12* (2013.01);
(Continued)

(58) Field of Classification Search
CPC ... A01C 1/08; A61L 2/26; A61L 2/087; A61L 2202/11; B01J 19/085; B01J 8/12;
(Continued)

(56) References Cited

U.S. PATENT DOCUMENTS 3,833,814 A * 9/1974 Nablo .................... H01J 33/00
                                                    250/398
4,782,267 A    11/1988 Collins et al.
(Continued)

FOREIGN PATENT DOCUMENTS

CN    103299390 A    9/2013
DE    23 34 106 A1    1/1975
(Continued)

OTHER PUBLICATIONS

International Search Report with English translation, dated Feb. 9, 2015, pp. 1-6, issued in International Patent Application No. PCT/EP2014/074378, European Patent Office, Rijswijk, The Nethrelands.

*Primary Examiner* — Michael Maskell
(74) *Attorney, Agent, or Firm* — Brinks Gilson & Lione (57) ABSTRACT

An apparatus includes at least one electron beam generator for generating accelerated electrons with which bulk material particles are impingeable during free fall. The electron beam generator has an annular design in which the electrons are emitted and accelerated by an annular cathode. The electrons exit from an electron outlet window in the direction of the ring axis. The annular electron beam generator is arranged in such a way that the ring axis of the electron beam (Continued)

generator is oriented perpendicular to, or at an angle of up to 45° from the horizontal. The apparatus may further include a device for separating bulk material particles arranged above the annular electron beam generator, the bottom wall of said device having at least one opening out of which the bulk material particles fall and, from there, fall through the ring which is formed by the electron beam generator.

13 Claims, 7 Drawing Sheets

(51) Int. Cl.
  *B01J 19/08* (2006.01)
  *H01J 37/00* (2006.01)
  *H01J 37/06* (2006.01)
  *A61L 2/08* (2006.01)
  *A61L 2/26* (2006.01)
(52) U.S. Cl.
  CPC ............ *B01J 19/085* (2013.01); *H01J 37/00* (2013.01); *H01J 37/06* (2013.01); *A61L 2202/11* (2013.01); *B01J 2219/0815* (2013.01); *B01J 2219/0833* (2013.01); *B01J 2219/0879* (2013.01); *H01J 2237/06375* (2013.01); *H01J 2237/15* (2013.01)
(58) Field of Classification Search
  CPC ........ B01J 2219/0815; B01J 2219/0879; B01J 2219/0833; H01J 37/00; H01J 37/06; H01J 2237/06375; H01J 2237/15

USPC ....................................... 250/453.11–455.11
See application file for complete search history.

(56) References Cited

U.S. PATENT DOCUMENTS

| | | | |
|---|---|---|---|
| 5,434,421 A | | 7/1995 | Burth et al. |
| 6,833,551 B2* | | 12/2004 | Avnery ................... G21K 5/10 250/492.1 |
| 8,698,097 B2* | | 4/2014 | Dally ..................... B01J 19/085 250/432 R |
| 2002/0149321 A1* | | 10/2002 | Avnery ................... G21K 5/10 315/169.3 |
| 2008/0267354 A1* | | 10/2008 | Holm ...................... H01J 33/00 378/122 |
| 2009/0184262 A1* | | 7/2009 | Bartel .................... A61L 2/087 250/492.3 |
| 2013/0162134 A1 | | 6/2013 | Mattausch et al. |
| 2015/0216106 A1* | | 8/2015 | Kotte ..................... A61L 2/087 47/58.1 R |

FOREIGN PATENT DOCUMENTS

| | | |
|---|---|---|
| DE | 291 704 B5 | 7/1991 |
| DE | 44 34 767 C1 | 2/1996 |
| DE | 199 42 142 A1 | 3/2001 |
| DE | 10 2009 034 646 A1 | 9/2010 |
| DE | 10 2012 209 434 A1 | 12/2013 |
| EP | 0 705 531 A2 | 4/1996 |
| FR | 2 235 755 A1 | 1/1975 |
| JP | 2003-294897 A | 10/2003 |
| WO | WO 98/43274 | 10/1998 |

* cited by examiner

APPARATUS FOR IMPINGING BULK MATERIAL WITH ACCELERATED ELECTRONS

CROSS-REFERENCE TO RELATED APPLICATIONS

This application is a 371 nationalization of PCT/EP2014/074378, entitled "VORRICHTUNG ZUM BEAUFSCHLAGEN VON SCHÜTTGUT MIT BESCHLEUNIGTEN ELEKTRONEN," having an international filing date of Nov. 12, 2014, the entire contents of which are hereby incorporated by reference, which claims priority under 35 USC § 119 to Germany patent application DE 10 2013 113 688.5 filed on Dec. 4, 2013, entitled "Vorrichtung zum Beaufschlagen von Schüttgut mit beschleunigten Elektronen," the entire contents of which are hereby incorporated by reference.

TECHNICAL FIELD

The invention relates to an apparatus for the treatment of bulk material, preferably of seeds, with accelerated electrons. The preferred field of application is the phytosanitary treatment of seeds against seed-borne pathogens that are predominantly located in the seed casings of the seeds. Further applications are surface sterilization of granulates and powders, chemical surface activation, as well as the performance of other radiochemical processes on bulk goods.

BACKGROUND

Various methods and the corresponding apparatuses are known in various embodiments—adapted to the bulk material to be treated—for impinging bulk material with accelerated electrons.

Thus an electron field having opposing velocity components of the electronics is generated in an evacuated chamber by opposing arrangement of two electron accelerators, through which electron field the bulk material is guided in free fall in an extended transparent stream (DD 291 702 A5). For the electron treatment, the bulk material is fed into the chamber via cellular wheel sluices and discharged again after the electron beam process. However, the disadvantage of such apparatuses is the high equipment expense for generating the electron field, since at least two electron accelerators are required, and the high expense of vacuum technology.

It is also known to generate an electron field having opposing velocity components such that the electron beam is diverted back to the particle stream by magnetic deflection after it has passed the bulk-material particles. Apparatuses of this type avoid the expense of a second electron accelerator. However, the disadvantage of this method consists in that, due to the relatively long path that the electron beam traverses in the process chamber, a substantially better vacuum is required, which requires an even greater equipment expense with respect to vacuum generation.

Methods and apparatuses are also known that work with two mutually opposing electron accelerators, wherein the electrons escape at atmospheric pressure via a beam-escape window (DE 44 34 767 C1). Here the bulk material is also guided in free fall through the electron field. In this solution the expense is omitted of the otherwise necessary evacuation of the process chamber. However, the disadvantage remains of the high equipment cost due to the required use of at least two electron accelerators.

It is furthermore known to impinge materials in powder form and materials in granular form with electrons at atmospheric pressure, wherein only one electron accelerator is sufficient for use and the to-be-irradiated particles are carried through the electron field in a gas stream (WO 98/43274 A1). The gas stream including the to-be-irradiated particles is guided through a rectangular channel, which is closed on one side with 25-μm-thick aluminum foil, through which the electrons penetrate after their discharge via a 13-μm-thick titanium window foil and pass the distance up to the radiating channel. Opposite the aluminum foil, the rectangular channel is formed by a flat plate made from a material of high atomic number. After penetrating the channel cross-section the electrons are backscattered from this plate to a certain component. The backscattered electrons have a velocity component opposing the original input direction of the electrons and make possible that the side of the particles facing away from original input direction of the electrons is also subjected to electron bombardment.

It is disadvantageous that the intensity of the irradiation by the backscattered electrons is significantly lower than the intensity of the irradiation by the electrons escaping directly from the beam escape window, which leads to an uneven irradiating of the individual particles. It is also disadvantageous that the gas velocity required for carrying the particles strongly increases with an increasing ratio of mass to the surface of the transported particles. Thus for large-grain bulk material—such as, e.g., wheat or corn—very high gas-flow velocities are required. At these high velocities the energy doses, transferable in the electron field are limited to very small—for numerous applications substantially too small— values. A further disadvantage of this known solution consists in that after escaping from the electron accelerator the electrons still must additionally penetrate the aluminum foil closing the rectangular channel before they encounter the to-be-treated particles. The electrons thereby suffer an additional undesired energy loss.

Finally in DE 199 42 142 A1 a device is disclosed wherein bulk material is guided in multiple free falls past an electron beam device and impinged with accelerated electrons. Due to the multiple traversals, in conjunction with a simultaneous mixing of the bulk material, the probability with this embodiment is very high that the particles of the bulk material are impinged on all sides by accelerated electrons. However the multiple traversals requires a large amount of time in the performing of the treatment process.

DETAILED DESCRIPTION

The object of the invention is therefore based on the technical problem of providing an apparatus for impinging bulk material with electrons, using which the disadvantages of the prior art can be overcome. In particular the apparatus should make possible more compact dimensions compared to the prior art and nonetheless permit a high throughput of to-be-treated bulk material.

An essential feature of an inventive apparatus consists in that it is configured ring-shaped, wherein the electrons are acceleratable in the direction of the interior of the ring. In this manner a substrate, which is guided through the ring interior of the apparatus, is impinged in an irradiation passage on all sides with respect to a substrate cross-section by accelerated electrons. At this point it is expressly referenced that the term "ring-shaped" in the sense of the invention is not limited to a ring in circular shape in all ring-shaped apparatuses and components described below, but that the term "ring-shaped" in the sense of the invention refers only to a self-contained loop-shaped object wherein the self-contained loop-shaped object completely encloses a free space in its cross-section, and wherein bulk material can be guided through this free space in the interior of the ring. Indeed here in a preferred embodiment of the invention the cross-section of the free space completely enclosed by a ring is configured circular, but in the broadest sense of the invention it can also have any other geometric shape.

In one embodiment of the invention, the ring-shaped electron beam generator is disposed such that the ring axis of the ring-shaped electron beam generated is oriented vertically. Alternatively, embodiment variants are also possible wherein the ring axis deviates up to 45° from vertical. Preferably the ring axis of the ring-shaped electron beam generator does not deviate by more than 10° from vertical. With a ring-shaped electron beam generator disposed in this way it is possible to allow bulk material to fall in free fall through the ring interior of the ring-shaped electron beam generator and impinge the bulk material with accelerated electrons during the free fall through the ring interior.

If it is to be ensured that the bulk material particle is impinged on all sides to the greatest extent possible by accelerated electrons, the bulk-material stream falling through the ring interior of the ring-shaped electron beam generator is preferably formed such that the bulk-material particles fall isolated through the ring interior. An inventive apparatus therefore also comprises, in addition to a ring-shaped electron beam generator, another device, disposed above the ring-shaped electron beam generator, for isolating the bulk-material particles, the lower limit of which device includes at least one opening from which the bulk-material particles fall out of and from there through the ring formed by the electron beam generator.

The device for isolating bulk material particles can comprise, for example, a container for receiving bulk material particles, wherein the base of the container includes at least one opening from which the bulk material particles can fall out. The opening is preferably dimensioned large enough that always only one bulk-material particle after another can fall through the opening in the base of the container. If the bulk-material particles have an approximately identical size, the size of the opening in the base of the container can be configured such that its diameter is smaller than twice the average diameter of the bulk-material particles. With the use of a circular ring-shaped electron beam generator, the ring axis of which is oriented vertically, the device for isolating bulk-material particles is preferably disposed above the electron beam generator such that the opening in the base of the container for receiving bulk-material particles is located on the extended ring axis of the electron beam generated. In this manner the bulk-material particles fall centrically through the electron beam generator and are impinged on all sides by an at least approximately equal energy dose.

With such an apparatus, in which always only one bulk-material particle after another falls through the ring interior of the ring-shaped electron beam generator, it can be ensured that the bulk-material particles are impinged on all sides by accelerated electrons. However, the throughput of bulk-material particles impinged by electrons is only slight.

In an alternative embodiment the base wall of a container for receiving and isolating bulk-material particles includes one or more openings that are not disposed at the position of the extended ring axis of the ring-shaped electron beam generator. A further feature of the base wall consists in that it is rotatably disposed or disposed such that it is movable within the horizontal plane.

In a further alternative embodiment, an inventive device comprises a circular ring-shaped electron beam generator whose ring axis is oriented vertically, as well as a device, disposed above the electron beam generator, for isolating bulk-material particles, which device includes a plurality of openings in the base wall. The openings in the base wall are preferably radially symmetric, each disposed with the same spacing on a circular path around the extended axis of the electron beam generator. Here the radius of the circular path whereon the openings are introduced in the base wall is smaller than the inner radius of the ring-shaped electron beam generator so that all bulk-material particles falling out of the openings of the base wall also fall through the ring opening of the ring-shaped electron beam generator. The openings in the base wall of the device for isolating the bulk-material particles are preferably configured large enough that only one bulk-material particle after another can ever fall through an opening.

In this manner a transparent, annular bulk-material stream—comprised of falling bulk-material particles—is generated, which falls through the ring opening of the ring-shaped electron beam generator and is impinged here by accelerated electrons. With respect to the ring-shaped stream of falling bulk-material particles, "transparent" means that adjacently falling bulk-material particles are each spaced from one another to such a degree that a plurality of electrons accelerated by the ring-shaped electron beam generator can also always pass between the falling bulk-material particles, which electrons then impinge on the opposite side of the ring-shaped, falling bulk-material stream on the back sides of the bulk-material particles oriented towards the ring axis, whereby with such an apparatus, the falling bulk-material particles are also impinged on all sides by accelerated electrons.

Alternatively a transparent, ring-shaped bulk-material stream—comprised of falling, isolated bulk-material particles—is generated by a ring-shaped opening being introduced in the base wall of a device, disposed above a ring-shaped electron beam generator, for isolating bulk-material particles. Here the ring opening is preferably formed radially symmetric around the extended ring axis of the ring-shaped electron beam generator. The gap width of the ring-shaped opening here is preferably dimensioned large enough that with respect to the gap width only one bulk-material particle passes through. In this manner a transparent, ring-shaped bulk-material stream of falling bulk-material particles is also generated having a ring width of a bulk-material particle.

It is also advantageous if with all above-mentioned exemplary embodiments at least one component of the device for isolating bulk-material particles is subjected to a vibration so that the at least one opening in the base wall of the device is not blocked by bulk-material particles. Thus, for example, the base wall of the device for isolating bulk-material particles or its lateral walls can be subjected to an oscillation and thus set in vibration. Oscillation generators usable for this purpose, which are brought into mechanical contact with a component of the device for isolating bulk-material particles, are known.

EXEMPLARY EMBODIMENTS

Figure 1:
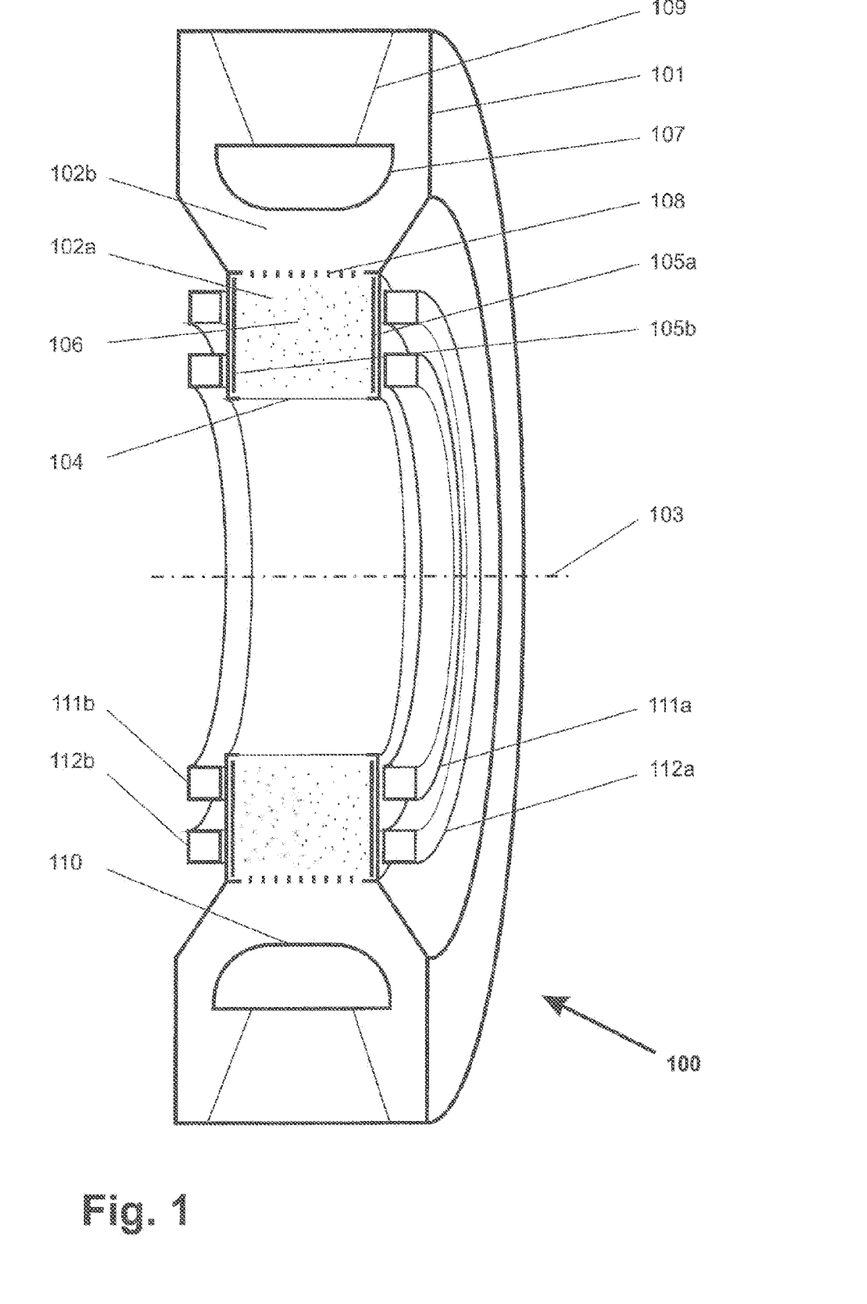
FIG. 1 a schematic and perspective sectional view of a ring-shaped electron beam generator including poloidal coils.
Figure 2:
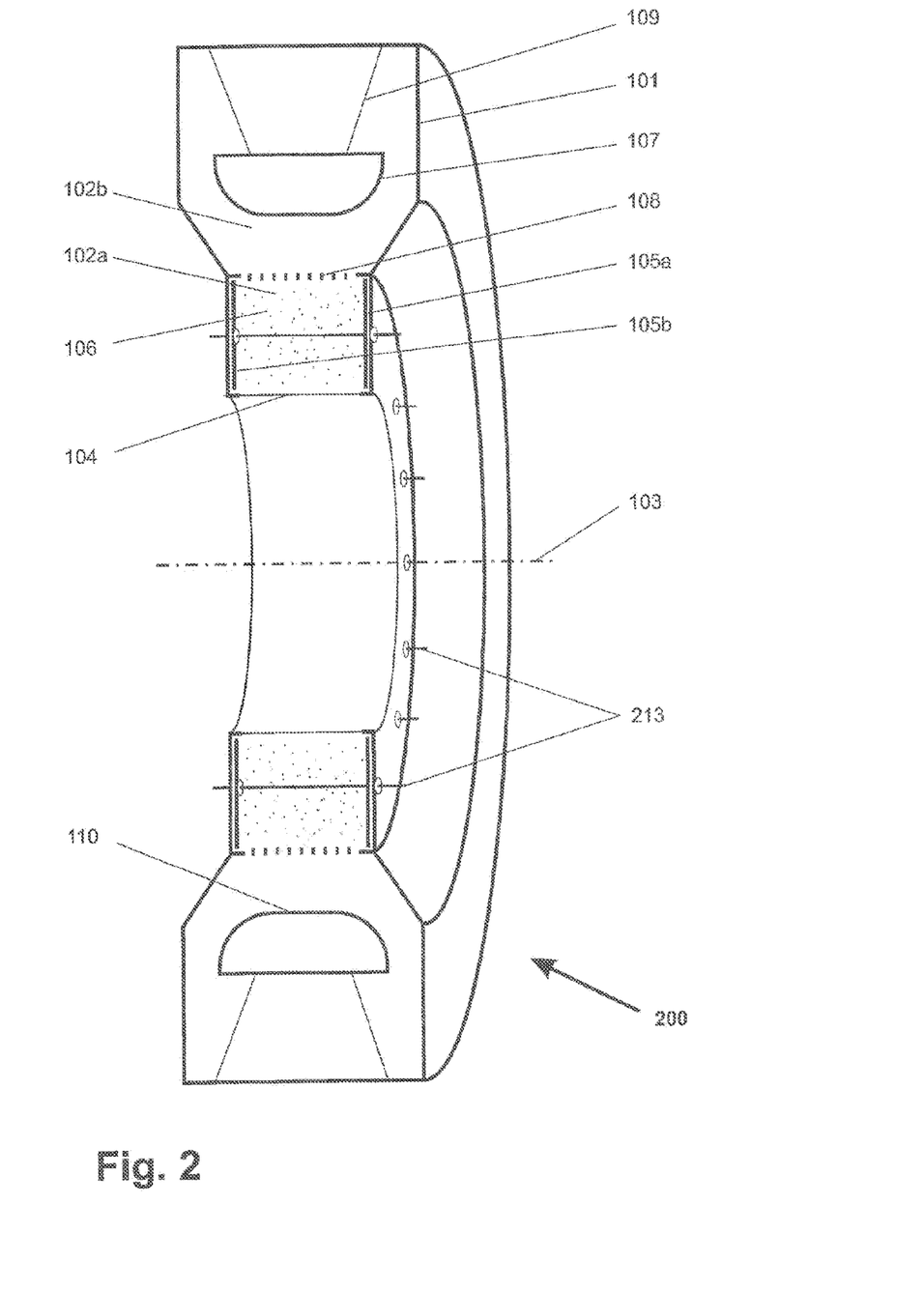
FIG. 2 a schematic and perspective sectional view of an alternative ring-shaped electron beam generator with anodic wire electrodes.
Figure 3:
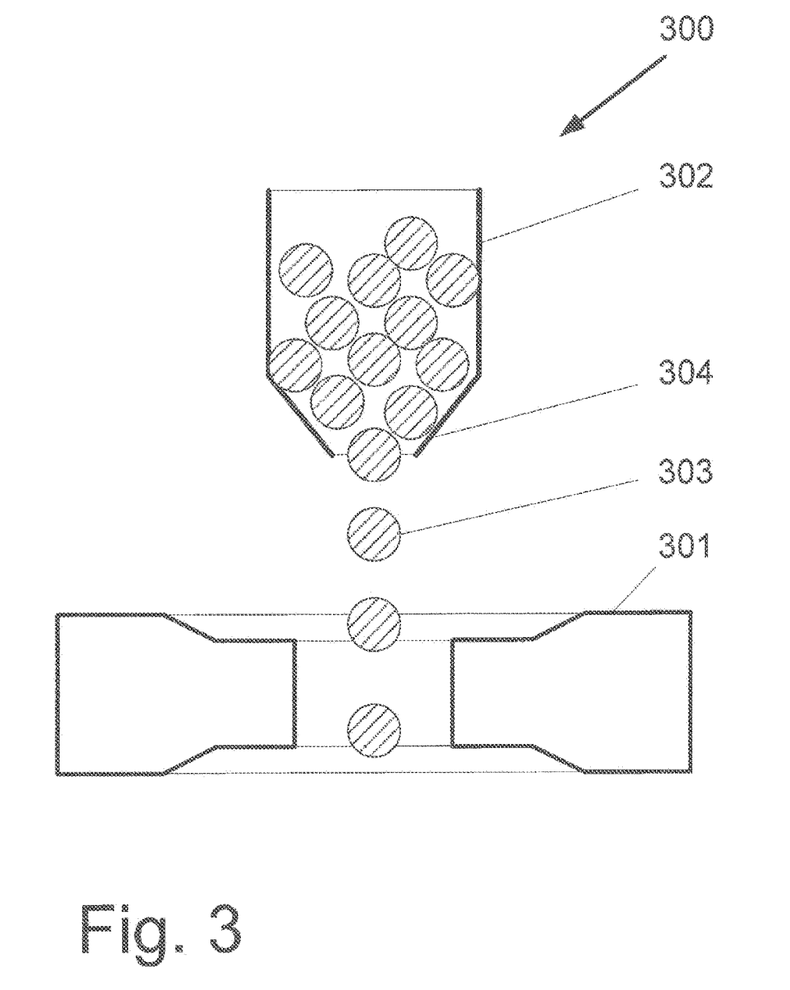
FIG. 3 a schematic sectional view of an inventive apparatus in cross-section.
Figure 4A:
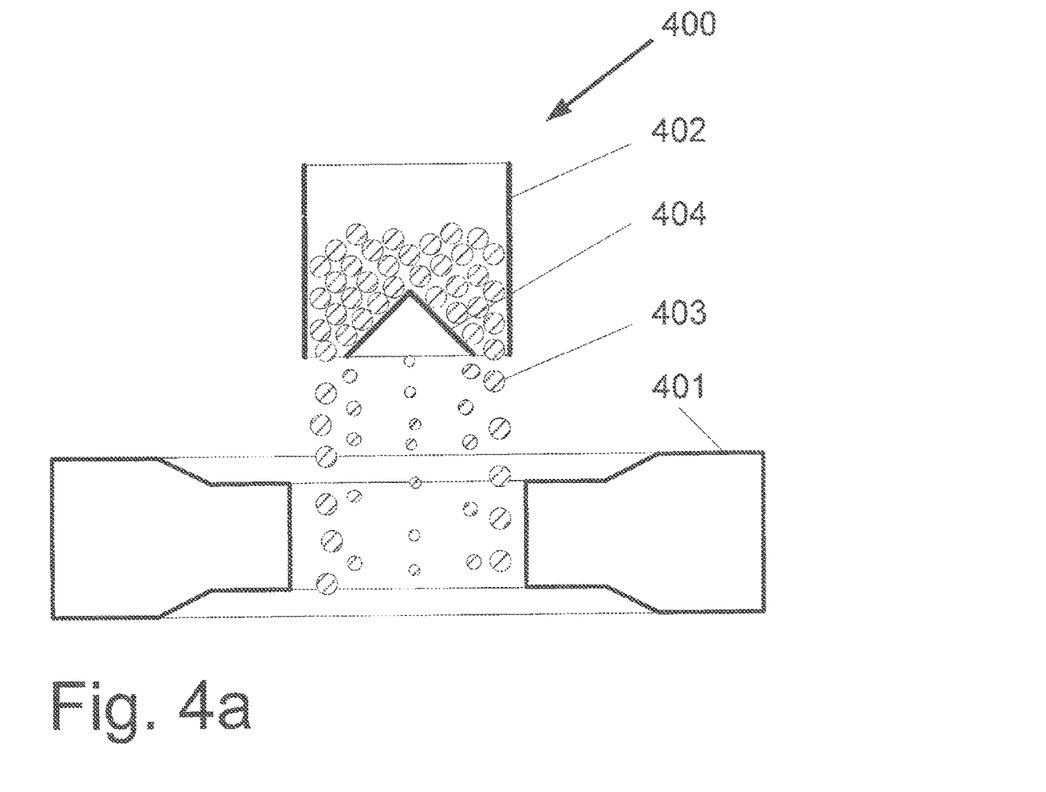
FIG. 4a a schematic sectional view of an alternative inventive apparatus in cross-section.
Figure 4B:
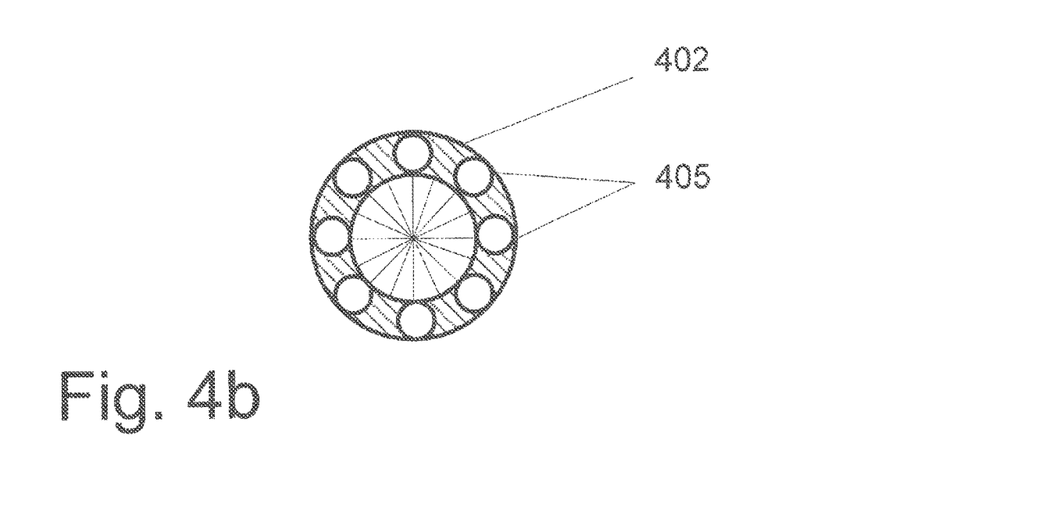
FIG. 4b shows a schematic depiction of a container for receiving bulk-material particles of the apparatus from FIG. 4a in plan view.
Figure 5A:
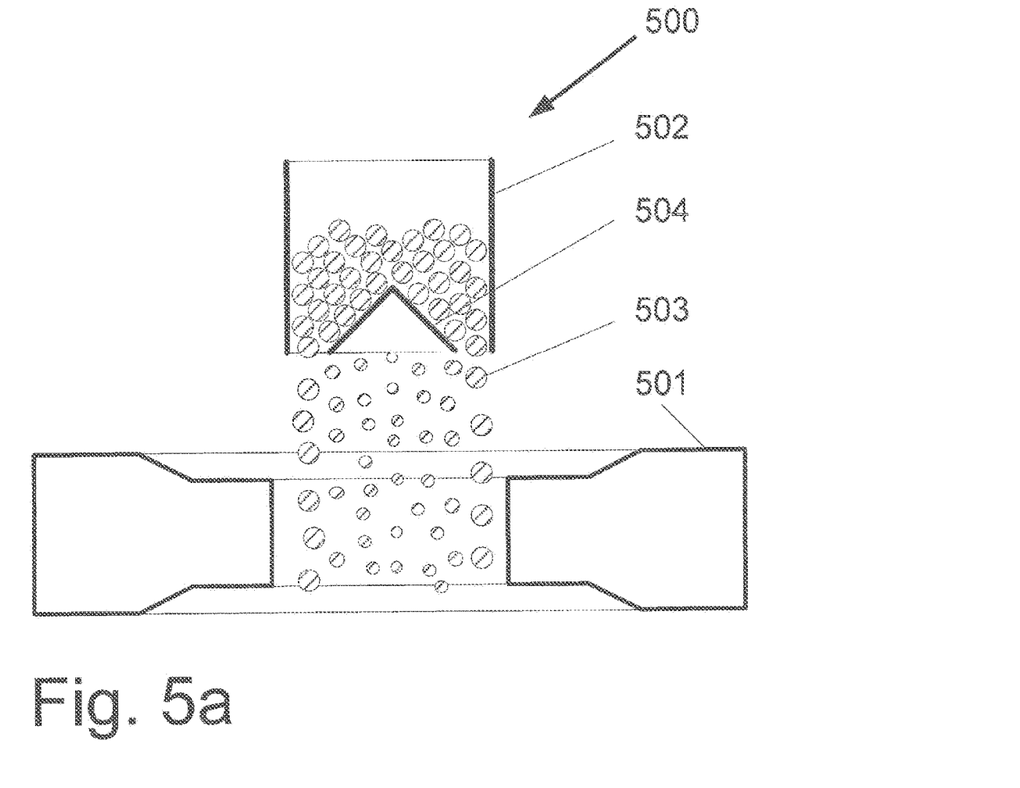
FIG. 5a a schematic sectional view of a further alternative inventive apparatus in cross-section.
Figure 5B:
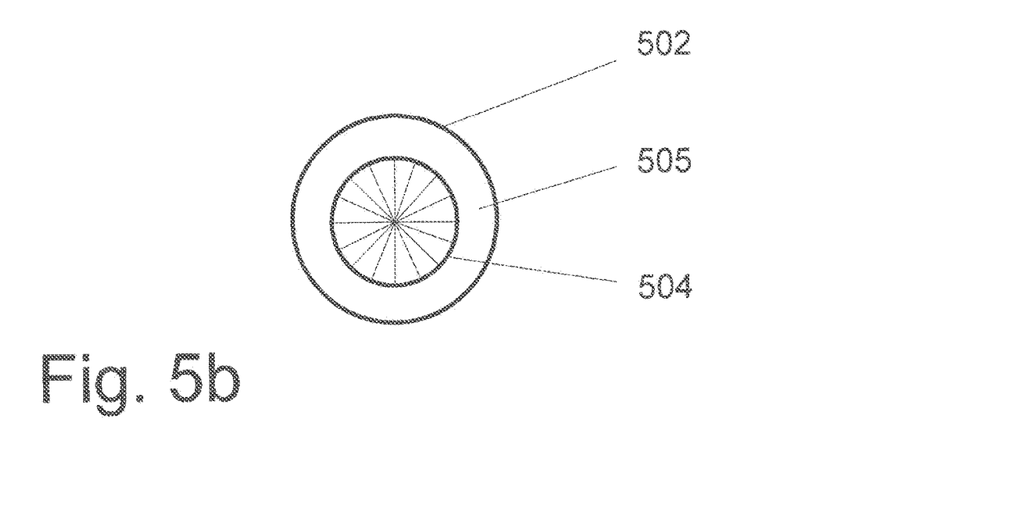
FIG. 5b a schematic depiction of a container for receiving bulk-material particles of the apparatus from FIG. 5a in plan view.
Figure 6:
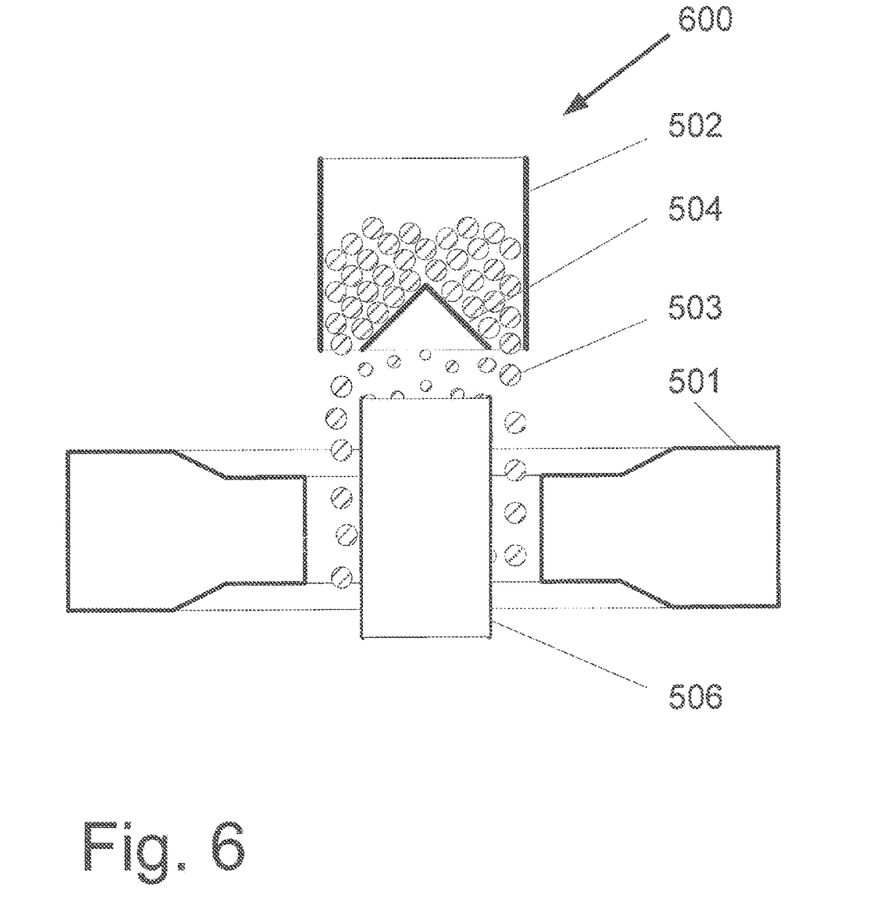
FIG. 6 a schematic sectional view of an inventive apparatus including an electron reflector.
Figure 7:
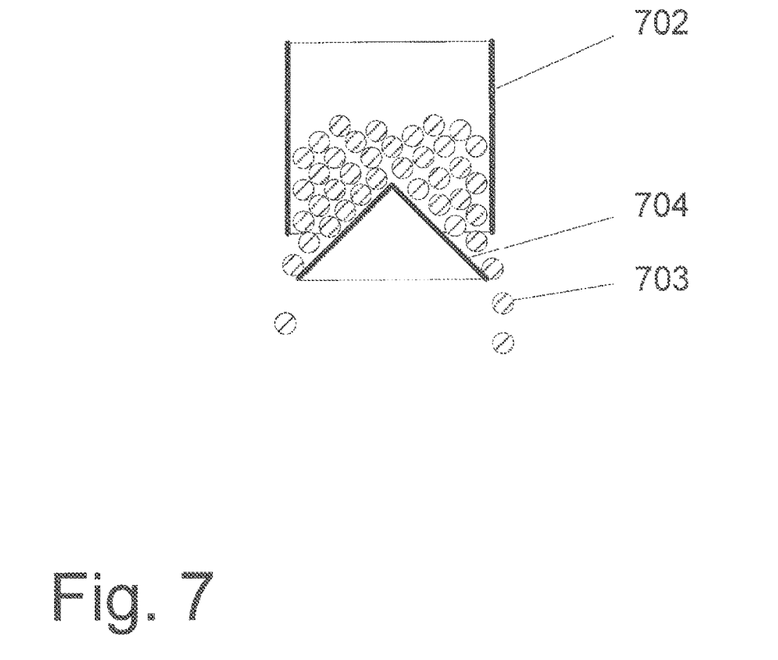
FIG. 7 a schematic sectional view of an alternative container for receiving bulk-material particles.

The invention is explained in more detail below with reference to exemplary embodiments. The Figures show:

FIG. 1 a schematic and perspective sectional view of a ring-shaped electron beam generator including poloidal coils;

FIG. 2 a schematic and perspective sectional view of an alternative ring-shaped electron beam generator with anodic wire electrodes;

FIG. 3 a schematic sectional view of an inventive apparatus in cross-section;

FIG. 4a a schematic sectional view of an alternative inventive apparatus in cross-section;

FIG. 4b shows a schematic depiction of a container for receiving bulk-material particles of the apparatus from FIG. 4a in plan view;

FIG. 5a a schematic sectional view of a further alternative inventive apparatus in cross-section;

FIG. 5b a schematic depiction of a container for receiving bulk-material particles of the apparatus from FIG. 5a in plan view;

FIG. 6 a schematic sectional view of an inventive apparatus including an electron reflector;

FIG. 7 a schematic sectional view of an alternative container for receiving bulk-material particles.

In FIGS. 1 and 2 in the first instance ring-shaped electron beam generators are schematically depicted, which can be used in an inventive apparatus. For better understanding at this point the terms "ring-cylinder" and "ring-disc" are defined with respect to a ring-shaped object. If the inner radius of a circular ring is subtracted from its outer ring, a dimension results. If this dimension is smaller than the extension of the ring in the direction of its ring axis, then the ring is configured as a ring-cylinder. However, if this dimension is larger than the extension of the ring in the direction of its ring axis, then the ring is configured as a ring-disc.

FIG. 1 shows a ring-shaped electron beam generator 100 as a schematic perspective sectional view. Such an electron beam generator comprises first of all a ring-shaped housing 101, which at least in one region delimits an evacuable space 102, which is divided into the evacuable spaces 102a and 102b. Due to the housing shape, this evacuable space 102 is likewise ring-shaped. In the exemplary embodiment of FIG. 1 the housing 101 is configured radially symmetric about a ring axis 103. All components described below belonging to the electron beam generator 100 and referred to as ring-shaped are also radially symmetric and have one and the same ring axis 103. The housing 101 is configured as an electron escape window 104 in the shape of a ring cylinder on the ring inside of the housing 101, i.e., viewed in the escape direction of the electrons, the electron escape window 104 has a surface perpendicular that is oriented towards the ring interior and towards the ring axis 103 in a circular ring-cylinder such as in the electron escape window 104. A working gas is introduced in the evacuable space 102 through at least one inlet, not depicted in FIG. 1, in the housing 101, and a vacuum is maintained in the evacuable space 102, in the range from 0.5 Pa to 1.5 Pa and preferably in the range from 0.9 Pa to 1.1 Pa, by at least one pump device also not depicted in FIG. 1.

The ring-shaped electron beam generator further includes at least one first cathode and at least one first anode, between which a glow-discharge plasma is generatable in the evacuable space 102 using a first applied electric voltage, which is provided by a first power-supply device. In the exemplary embodiment, two first cathodes 105a and 105b configured as ring-discs were used, which are oppposingly disposed in the space 102 in the vicinity of the lateral inner walls of the housing 101. In the electron beam generator 100 the housing 101 was further connected as the first anode, wherein the housing 101 simultaneously has the electric ground potential of the electron beam generator 100. Alternatively at least one separate electrode can be connected as the first anode, which is electrically isolated from the housing 101. The ring-shaped first cathodes 105a and 105b are spaced from the respective adjacent walls of the housing 101 by a small enough distance that, due to the dark field shielding, no electric charge is formed between the cathodes 105 and the directly adjacent walls of the housing 101 connected as the first anode. A first electric voltage applied between the housing 101, connected as first anode, and the first cathode 105, thus causes a glow discharge to be formed between a first cathode 105a, 105b and a respective opposing wall of the housing 101. A plasma 106 generated in this manner thus fills the space 102a between the two first cathodes 105a and 105b.

A ring-shaped electron beam generator further comprises at least one second cathode and at least one second anode, between which a second electrical voltage is connected using a second power supply device. In the electron beam generator 100 a ring-shaped cathode 107 is configured as a second cathode and a ring-shaped and simultaneously lattice-shaped anode 108 is configured as a second anode.

In a ring-shaped electron beam generator, the second cathode represents the cathode for emitting secondary electrons, which are subsequently accelerated and for this purpose have an electric high-voltage potential of at least −50 kV, preferably in the range from −100 kV to −300 kV. The second cathode 107 is electrically isolated with respect to the housing 101 by an isolator 109.

In the embodiment described in FIG. 1 of a ring-shaped electron beam generator, the second anode 108 and the first cathodes 105a, 105b have the same electric potential, which is only a small percentage of the voltage potential of the second cathode 107 and is preferably selected from the range of −0.5 kV to −5 kV. Alternatively the second anode and the first cathode can also have different electric potentials, wherein, however, the two voltage potentials have a significantly lower voltage difference to the first anode than to the second cathode.

Ions drift from the plasma 106 in the space 102a through the lattice-shaped second anode 108 towards the second cathode 107. There the ions impinge on a surface region 110 of the second cathode 107 whose surface perpendicular is oriented towards the ring interior of the housing, and towards ring axis 103 in a radially symmetric housing such as housing 101. When the ions impinge on the surface region 110 the ions have thus fallen through a potential difference that essentially corresponds to the acceleration voltage of the electron beam generator 100. Upon their impinging, the energy of the ions are released in a very thin edge layer of the cathode 107 in the surface region 110, which leads to the release of secondary electrons. With the above-mentioned electrical voltage at the second cathode 107, the ratio between released electrons and impinging ions is established on the scale of 10, which makes this manner of generating accelerated electrons very efficient. The accrued secondary electrons are strongly accelerated by the applied electric field and fly through the lattice-shaped anode 108 configured in the shape of a ring-cylinder and the plasma 106 in the space 102a. After the traversing of the electron escape window 104, which can be embodied, for example, as thin metal foil, the electrons advance into the free space enclosed by the ring-shaped housing 101, wherein a higher pressure can prevail than in the space 102 and through which a bulk material to be impinged by electrons can fall. All materials known from the prior art for an electron escape window can be used as material for the electron escape window 104, such as, for example, titanium. Furthermore for the purpose of a high mechanical stability of the electron escape window 104, it is advantageous to provide it with a support lattice, as is also known from the prior art. Due to the ring-shaped design of all above-mentioned components of a ring-shaped electron beam generator, a closed, ring-shaped band of accelerated electrons is generated therewith, wherein the movement direction of the accelerated electrons is directed on the free space enclosed by the housing ring. The free space, which is enclosed by the housing ring and through which a to-be-treated bulk material falls, is referred to below as the treatment space. In a radially symmetric ring-shaped electron beam generator, such as electron beam generator 100, the movement direction of the accelerated electrons is preferably directed to the ring axis 103. Isolated bulk material, which falls through the ring interior of the housing of such a ring, can thus be impinged on all sides by accelerated electrons in a pass-through.

For the sake of completeness it is mentioned at this point that a ring-shaped electron beam generator also includes a device for cooling as is also known in other devices from the prior art for generating accelerated electrons. Thus this device for cooling a ring-shaped electron beam generator can comprise cooling channels, for example, which extend inside the insulator 109 and through which a cooling medium flows.

The second anode 108, which in a ring-shaped electron beam generator is preferably configured as a lattice-shaped ring-cylinder and which represents the spatial boundary between the evacuable spaces 102a and 102b, fulfills two significant functions. On the one hand, due to its voltage difference with respect to the second cathode 107 it effects an acceleration of the emitted secondary electrons. Due to the fact that the ring-shaped lattice structure of the second anode 108 is configured parallel to the surface 110 of the second cathode 107, which surface 110 emits secondary electrons, an electric field is formed such that the paths of the accelerated secondary electrons also extend substantially parallel. On the other hand the second anode 108 shields the plasma from the voltage potential of the second cathode 107; it thereby prevents the drifting of too many ions towards second cathode 107 and thus contributes to maintaining the plasma 106 in the space 102a.

However, for the maintenance of the plasma 106 still further measures are required. The relatively low pressure of approximately 1 Pa in space 102a makes possible only the generating of a relatively small number of low-energy electrons due to the glow discharge between the first cathode 105 and the housing 101 connected as first anode. The drifting of these low-energy electrons on the direct path between a first cathode 105 and the first anode would only lead to an insufficient number of impact reactions with inert gas particles and thus to the generating of ions, which would not be sufficient to maintain the plasma 106. Measures are thus necessary that extend the path of the low-energy electrons in space 102a and thus increase their impact probability and impact frequency.

One such measure is depicted in FIG. 1 in the form of ring-shaped magnetic coils 111a, 111b, 112a, 112b, which each generate a magnetic field having poloidally extending magnetic field lines. Such magnetic coils are thus also referred to as poloidal coils. The magnetic coils 111a, 111b, 112a, 112b are disposed in two pairs opposingly and outside the housing 101 at the height of the first cathode 105 such that their magnetic field penetrates the space 102a. Here the magnetic coils 111a and 111b have identical ring radii, which are larger than the identical ring radii of the magnetic coils 112a and 112b. The poloidally extending magnetic field lines in the space 102a compel the low-energy electrons onto curved paths having energy-dependent gyration radius, which increases the drift distance and thus also the time spent by the low-energy electrons in space 102 and thus the number of ion-generating impact events.

However, the magnetic fields of the magnetic coils 111a, 111b, 112a, 112b influence not only the paths of the low-energy electrons, but also the paths of the high-energy electrons emitted from the second cathode 107 and subsequently accelerated, as well as the electrons flying through the space 102a. Without the magnetic fields of the magnetic coils 111a, 111b, 112a, 112b most of the accelerated, high-energy electrons would pass through the electron escape window 104 at a perpendicular angle or at an angle close to the perpendicular angle. However, the magnetic fields of the magnetic coils 111a, 111b, 112a, 112b change this pass-through angle, which can be advantageous or disadvantageous depending on the application case. This is advantageous, for example, in homogenization of the energy input in the substrate with curved surface regions or for impinging of surface regions of a substrate which would be found in shaded surface regions in the case of a purely radial propagation direction of the accelerated electrons.

However, in many applications it is advantageous if the passage of accelerated electrons through the electron escape window 104 occurs at a right angle to the surface of the electron escape window 104 or at an angle close to the right angle. In addition, any deviation from normal incidence leads to a higher absorption of electrons in the foil of the electron escape window 104 and in particular also in the usually-supporting-and-cooling lattice structure of the electron escape window. In the application cases where in the accelerated electrons should pass through the electron escape window 104 as perpendicular as possible, with the use of magnetic coils 111a, 111b, 112a, 112b a correction of the flight path of the accelerated electrons is therefore required.

The deflecting of the flight paths of accelerated electrons resulting from the magnetic fields of the magnetic coils 111a, 111b, 112a, 112b can, for example, be compensated for using an additional pair of opposingly disposed poloidal coils, wherein the additional pair of poloidal coils has an outer radius that is even smaller than the inner radius of the magnetic coils 111a, 111b. Here, however, the inner radii of all three ring-shaped magnetic coil pairs is preferably greater than the outer radius of the cylindrical electron escape window 104, and the outer radii of all of the ring-shaped magnetic coil pairs are smaller than the inner radius of the lattice-shaped second anode 108. In this manner it is ensured that the magnetic fields of the ring-shaped magnetic coils inside an inventive apparatus mainly extend in the space 102a and contribute there to maintaining the plasma or to correcting the flight path of the accelerated electrons.

Alternatively, however, depending on the application case, another arrangement of the magnetic coils is also possible. Favorable values for number, position, and excitation of the magnetic coils for a respective application counter-attachment structure can be found, for example, using simulation calculations.

A further solution for extending the drift paths of low-energy electrons between the first cathode and the first node is indicated FIG. 2. In FIG. 2 an alternative ring-shaped electron beam generator 200 is shown as a schematic perspective sectional depiction, which initially comprises identical components and features of the electron beam generator 100 from FIG. 1, except for the magnetic coils 111a, 111b, 112a, 112b. Instead of the magnetic coils, electron beam generator 200 includes a number of wire-shaped electrodes 213, which extend through the space 102a and are disposed in a housing around the axis 103 in the form of a circular ring, such as housing 101, at an identical radius and with an identical spacing to one another. Thereby, the wire-shaped electrodes 213, which can have a slightly positive voltage potential in a range from +0.5 kV to +5.0 kV with respect to the housing 101, are electrically isolated by the housing 101 and pass through the first cathodes 105a, 105b. Due to the wire-shaped electrodes 213, the low-energy electrons are also turned in the space 102a on spiral-shaped and thus extended paths, and thus maintain the plasma 106.

In order to minimize the development of ozone and nitrogen oxides, the flushing of the treatment space with a noble gas is recommended, whereby a cooling effect on the to-be-treated bulk material and on the electron escape window simultaneously arises. In this context it is also conceivable to additionally influence the energy input in a bulk material to be impinged by accelerated electrons, which bulk material falls through the treatment space, through a suitable selection or mixture of different gases in the treatment space, since the energy absorption and electron scattering on the gas path between electron escape window and the to-be-impinged surface of the bulk material depends on the mass density of the local atmosphere.

The regulation of the ancillary discharge between first cathode and first anode, via the intensity of which the electron beam power of a ring-shaped electron beam generator can be regulated, can be achieved in various ways. In addition to the gas flow in the electron beam generator, the ancillary discharge voltage between first cathode and first anode as well as the current through the ring-shaped magnetic coils are to be considered here as regulating variables. In an exemplary embodiment including wire-shaped electrodes 213, the pressure in space 102 and the electric voltage of the wire-shaped electrodes 213 can be selected as complementary regulating variables. It is to be noted here that the electrical regulating variables generally have shorter time constants and thus on the one hand can serve for more rapid regulation, and on the other hand make possible a pulsed operating mode.

FIG. 3 shows a schematic sectional view of an inventive apparatus 300. Apparatus 300 comprises a ring-shaped electron beam generator 301 whose ring axis is oriented vertically. The ring axis lies on the sectional plane depicted in FIG. 3. An apparatus for isolating bulk material particles is disposed above the electron beam generator 301. The apparatus for isolating bulk material particles comprises a cylindrical container 302, wherein bulk material particles 303 are located. The base wall 304 of the container 302 is configured cone-shaped, with the cone tip directed downward. The cone tip is positioned precisely on the extended ring axis of the ring-shaped electron beam generator 301. On the cone tip, the base wall 304 of the container 302 includes an opening of such a size that always only one particle after another can fall from the container 302 and from there can fall centrically through the ring opening of the ring-shaped electron beam generator 301. During the falling-through through the ring opening of the electron beam generator 301, the bulk material particles are impinged on all sides by accelerated electrons from the electron beam generator 301. The device for isolating the bulk-material particles 303 further comprises a means, not shown in FIG. 3, by which the bulk material particles 303 can be refilled into the container 302. Furthermore, the device for isolating bulk material particles can comprise an oscillation generator, also not shown in FIG. 3, which has a mechanical contact with the container 302 whereby the container 302 vibrates.

It was previously stated that the size of the opening in the base wall of the container 302 is preferably dimensioned such that, if possible, only one bulk material particle after another can fall through the opening. Such an embodiment is in particularly suitable if only the surface of bulk material particles are impinged with accelerated electrons, but the entire bulk material particle is not to be completely penetrated by electrons, as is the case, for example, in the treatment of seeds.

However, if there is a task to be performed of completely penetrating bulk material particles with accelerated electrons, such as, for example, in the modification of plastic particles, the opening in container 302 can also be dimensioned larger so that several bulk material particles 303 can fall through the opening simultaneously. This application-based statement with respect to the size of the opening in the base wall of a container for receiving bulk material particles is also usable in all embodiments described below.

In FIG. 4a an alternative inventive apparatus 400 is schematically depicted in section. Apparatus 400 comprises a ring-shaped electron beam generator 401 whose ring axis is oriented vertically. The ring axis lies on the sectional plane depicted in FIG. 4a. An apparatus for isolating bulk material particles is disposed above the electron beam generator 401. The apparatus for isolating bulk material particles comprises a cylindrical container 402, wherein bulk material particles 403 are located. The container 402 is schematically depicted in FIG. 4b as a plan view. The base wall 404 of the container 402 is configured cone-shaped in a central region, with the cone tip directed upward. The cone tip is positioned precisely on the extended ring axis of the ring-shaped electron beam generator 401. Due to the cone shape of the central region of the base wall 404, the bulk material particles 403 in the lower region of the container 402 are urged to a ring-shaped outer area of the base wall 404 that includes a plurality of openings 405. The openings 405 are disposed in a rotationally symmetric manner about the extended ring axis of the ring-shaped electron generator 401 and each spaced the same distance from an adjacent opening 405. Each of the openings 405 is only large enough that one bulk material particle 403 after the other can fall through an opening 405.

Using such an apparatus for isolating bulk material particles, a bulk material stream comprised of falling bulk material particles 403 is generated that is transparent, ring-shaped, and disposed in a rotationally symmetric manner about the ring axis of the electron beam generator 401, which bulk material stream falls through the ring opening of the ring-shaped electron beam generator 401 and is impinged by accelerated electrons during the free fall. Using such an apparatus, wherein a ring-shaped, transparent bulk material stream is generated, which is impinged by accelerated electrons of a ring-shaped electron-stream generator, more compact system dimensions can be realized than with an apparatus from the prior art, wherein an identical-length, transparent, linear bulk material stream is impinged with accelerated electrons from linear emitters. A further advantage of the inventive apparatuses compared to the prior art, wherein two opposingly disposed linear emitters are used, consists in that only one electron beam generator is used. Thus in an inventive apparatus, only one set of peripheral equipment (such as, for example, vacuum pumps and power supply devices) is needed, whereas, in the prior art, two sets of peripheral equipment are respectively needed.

The device for isolating the bulk material particles 403 further comprises a means not shown in FIG. 4 by which the bulk material particles 403 are refilled in the container 402. Furthermore, the device for isolating bulk material particles can comprise at least one oscillation generator, also not shown in FIG. 4, which has a mechanical contact with the container 402 whereby the container 402 vibrates.

A further alternative inventive apparatus 500 is schematically depicted in section in FIG. 5a. Apparatus 500 comprises a ring-shaped electron beam generator 501 whose ring axis is oriented vertically. The ring axis lies on the sectional plane depicted in FIG. 5a. An apparatus for isolating bulk material particles is disposed above the electron beam generator 501. The apparatus for isolating bulk material particles comprises a container for receiving bulk material particles 503. The container is comprised of a cylindrical side wall 502 and a cone-shaped base wall 504, wherein a ring-shaped gap 505 is formed between the side wall 502 and the base wall 504. The container is schematically depicted in FIG. 5b as a plan view. The cone tip of the base wall is directed upward and positioned precisely on the extended ring axis of the ring-shaped electron beam generator 501. Due to the cone shape of the base wall 504, the bulk material particles 503 in the lower region of the cylinder 502 are urged to a ring-shaped outer region wherein the bulk material particles fall through the opening in the form of the ring gap 505. The ring gap is disposed rotationally symmetrically around the extended ring axis of the ring-shaped electron beam generator 401, and has a gap width such that with respect to the gap width only one bulk material particle 503 after another can fall through the ring gap 505. Of course viewed along the length of the ring gap 505 a plurality of bulk material particles 503 can fall simultaneously through the ring gap 505.

Using this device for isolating bulk material particles, a bulk material stream comprised of falling bulk material particles 503 is generated that is transparent, ring-shaped, and disposed in a rotationally symmetric manner about the ring axis of the electron beam generator 501, which bulk material stream falls through the ring opening of the ring-shaped electron beam generator 501 and is impinged by accelerated electrons during the free fall. Compared to an apparatus 400 from FIG. 4a, the ring-shaped bulk material stream generated by an apparatus 500 can be formed with a higher particle density with respect to its ring angular size and thus makes possible a higher bulk material throughput.

The device used here for isolating the bulk material particles 503 also comprises means, not shown in FIG. 5a, by which the bulk material particles 503 are refilled in the cylinder 502. Furthermore, this device for isolating bulk material particles can comprise at least one oscillation generator, also not shown in FIG. 5a, which has a mechanical contact with the cylinder 502 and/or the base wall 504, whereby these components vibrate and thereby ensure a continuously falling bulk material stream.

In FIG. 6 a further inventive apparatus 600 is schematically depicted in section, which first of all includes all features of the apparatus 500 from FIG. 5a. In addition, the apparatus 600 includes a cylindrical electron reflector 506 that extends through the ring opening of the ring-shaped electron beam generator 501. Here the cylindrical electron reflector 506 is formed rotationally symmetric about the ring axis of the ring-shaped electron beam generator and has a radius that is smaller than the radius of the transparent, ring-shaped bulk material stream comprised of falling bulk material particles 503. Using the cylindrical electron reflector 506, the accelerated electrons, which pass through the transparent ring-shaped bulk material stream, can be reflected and the falling bulk material particles 503 can thereby be impinged on their rear side oriented towards the ring axis.

In a further embodiment the cylindrical electron reflector 506 is divided into segments with respect to its ring angular size, wherein each segment is electrically contacted and connected to an evaluating unit by electrical connecting elements. In this way for each segment a value is captured that corresponds to the number of electrons impinging on the segment. Thus, for example, a value for the electric current can be captured for each segment. Such an embodiment can be used, for example, for quality assurance, since a qualitative statement can this be made as to whether different ring angle segments of the transparent ring-shaped bulk material stream were impinged with an at least approximately identical energy dose. If, in such a device configuration, an additional electron beam generator is also used whose second cathode is configured segmented, or an electron beam generator that includes wire-shaped electrodes 213, then the ring-shaped electron beam of the ring-shaped electron beam generator can be regulated by segment such that possible differences in the electron stream that are captured at different segments of the cylindrical electron reflectors can be balanced out. Thus, a uniform impinging of the ring-shaped bulk material stream can be ensured over the entire ring circumference.

Such a cylindrical electron reflector 506, whether segmented or not segmented, can be used in all embodiments of the invention wherein a ring-shaped, falling bulk material stream is generated, such as, for example, also in an embodiment according to FIG. 4a.

An alternative embodiment of a container for receiving bulk material particles 703 is depicted schematically in section in FIG. 7. The container is comprised of a cylindrical side wall 702 and a cone-shaped base wall 704 wherein a ring-shaped gap is formed between the side wall 702 and the base wall 704. The cone tip of the base wall 704 is oriented upward and positioned precisely along the extended ring axis of the associated ring-shaped electron beam generator. Due to the conical shape of the base wall 704, the bulk material particles 703 in the lower region of the cylinder 702 are urged to a ring-shaped outer region wherein the bulk-material particles fall out through the opening in the form of a ring gap. The base wall 704 and/or the cylindrical side wall 702 are configured height-adjustable. The width of the ring gap between side wall 702 and base wall 702 can thus be set and adapted to any size of bulk material particle 703.

The invention claimed is:

1. An apparatus comprising at least one electron beam generator for generating accelerated electrons with which bulk material particles are impingeable during free fall, wherein
the at least one electron beam generator is ring-shaped and has a ring axis, wherein the at least one electron beam generator comprises two first cathodes configured as ring-discs between which a glow-discharge plasma is generatable, and wherein the at least one electron beam generator comprises a second ring-shaped cathode configured to emit and accelerate electrons that pass through the glow-discharge plasma and escape from an electron escape window in a direction of the ring axis;
the at least one ring-shaped electron beam generator is disposed such that the ring axis is oriented vertically or with an angle deviating from vertical by up to 45°; and
the apparatus further comprises a device for isolating bulk material particles disposed above the at least one ring-shaped electron beam generator, a base wall of the device includes at least one opening from which the bulk material particles fall out and, from there, fall through a ring formed by the at least one electron beam generator.

2. The apparatus according to claim 1, wherein the at least one opening has a size such that always only one bulk material particle after the other falls through the at least one opening.

3. The apparatus according to claim 2, wherein the at least one opening is disposed on the position of the extended ring axis of the at least one ring-shaped electron beam generator.

4. The apparatus according to claim 2, wherein the lower base wall includes a plurality of openings, which are disposed concentrically around the extended ring axis of the at least one ring-shaped electron beam generator.

5. The apparatus according to claim 1, wherein the at least one opening is ring-shaped around the extended ring axis of the at least one ring-shaped electron beam generator.

6. The apparatus according to claim 5, wherein the at least one opening has a ring width such that with respect to the ring width only one bulk material particle passes through.

7. The apparatus according to claim 1, wherein the base wall comprises a cone-shaped element whose cone tip is disposed at the position of the extended ring axis of the at least one ring-shaped electron beam generator.

8. The apparatus according to claim 1, wherein at least one oscillation generator that has a mechanical contact with at least one component of the device for isolating bulk material particles.

9. The apparatus according to claim 1, wherein at least one component of the device for isolating bulk material particles is configured height-adjustable.

10. The apparatus according to claim 1, wherein at least one cylindrical electron reflector that extends through the ring opening of the at least one ring-shaped electron beam generator.

11. An apparatus comprising at least one electron beam generator for generating accelerated electrons with which bulk material particles are impingeable during free fall, wherein
the at least one electron beam generator is ring-shaped and has a ring axis, wherein the electrons emitted and accelerated by a ring-shaped cathode escape from an electron escape window in a direction of the ring axis;
the at least one ring-shaped electron beam generator is disposed such that its ring axis is oriented vertically or with an angle deviating from vertical by up to 45°; and
the apparatus further comprises a device for isolating bulk material particles disposed above the at least one ring-shaped electron beam generator, a base wall of the device includes at least one opening from which the bulk material particles fall out and, from there, fall through a ring formed by the at least one electron beam generator, wherein the at least one opening has a size such that always only one bulk material particle after the other falls through the at least one opening, and wherein the lower base wall includes a plurality of openings, which are disposed concentrically around the extended ring axis of the at least one ring-shaped electron beam generator.

12. An apparatus comprising at least one electron beam generator for generating accelerated electrons with which bulk material particles are impingeable during free fall, wherein
the at least one electron beam generator is ring-shaped and has a ring axis, wherein the electrons emitted and accelerated by a ring-shaped cathode escape from an electron escape window in a direction of the ring axis;
the at least one ring-shaped electron beam generator is disposed such that its ring axis is oriented vertically or with an angle deviating from vertical by up to 45°; and
the apparatus further comprises a device for isolating bulk material particles disposed above the at least one ring-shaped electron beam generator, a base wall of the device includes at least one opening from which the bulk material particles fall out and, from there, fall through a ring formed by the at least one electron beam generator, wherein at least one cylindrical electron reflector that extends through the ring opening of the at least one ring-shaped electron beam generator.

13. The apparatus according to claim 1, wherein the first two cathodes are configured as ring-discs having opposing surfaces that are perpendicular to the ring axis.

* * * * *